(12) United States Patent
Niihara

(10) Patent No.: US 10,258,586 B2
(45) Date of Patent: *Apr. 16, 2019

(54) METHODS AND COMPOSITIONS FOR THE TREATMENT OF DIVERTICULOSIS

(71) Applicant: Emmaus Medical, Inc., Torrance, CA (US)

(72) Inventor: Yutaka Niihara, Rolling Hills Estates, CA (US)

(73) Assignee: Emmanus Medical, Inc., Torrance, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/530,630

(22) Filed: Feb. 10, 2017

(65) Prior Publication Data

US 2017/0157080 A1    Jun. 8, 2017

Related U.S. Application Data

(63) Continuation of application No. 13/694,592, filed on Dec. 14, 2012, now Pat. No. 9,616,041.

(60) Provisional application No. 61/630,831, filed on Dec. 19, 2011.

(51) Int. Cl.
| | | |
|---|---|---|
| *A61K 31/198* | (2006.01) |
| *A61K 31/717* | (2006.01) |
| *A61K 31/721* | (2006.01) |
| *A61K 36/68* | (2006.01) |
| *A23L 33/24* | (2016.01) |
| *A23L 33/10* | (2016.01) |
| *A23L 33/00* | (2016.01) |
| *A23L 33/175* | (2016.01) |
| *A23L 33/105* | (2016.01) |

(52) U.S. Cl.
CPC .......... *A61K 31/198* (2013.01); *A23L 33/10* (2016.08); *A23L 33/105* (2016.08); *A23L 33/175* (2016.08); *A23L 33/24* (2016.08); *A23L 33/30* (2016.08); *A61K 31/717* (2013.01); *A61K 31/721* (2013.01); *A61K 36/68* (2013.01); *A23V 2002/00* (2013.01)

(58) Field of Classification Search
CPC .................................................... A61K 31/198
USPC ......................................................... 514/563
See application file for complete search history.

(56) References Cited

U.S. PATENT DOCUMENTS

| | | | |
|---|---|---|---|
| 2004/0005304 A1 | 1/2004 | Brudnak | |
| 2004/0096479 A1 | 5/2004 | Levine | |
| 2005/0058671 A1* | 3/2005 | Bedding | A61K 31/195 424/400 |
| 2007/0116837 A1 | 5/2007 | Prakash et al. | |
| 2008/0003265 A1 | 1/2008 | Casey et al. | |

OTHER PUBLICATIONS

Galera et al. Nutrition (2010), vol. 26, pp. 375-381 (Year: 2010).*
West (J. Clin.Gastroenterol. (2008), vol. 42, pp. 1137-1138). (Year: 2008).*
Glutasolve® online Retrieved from the internet Retrieved on Mar. 12, 2018 <url: http://www.nestlenutritionstore.com:80/departments/digestive-nutrition/adult-specialized-gi-nutrition/glutasolve> Sanpshot from the way back machine dated :Oct. 6, 2011 (Year: 2011).*

\* cited by examiner

*Primary Examiner* — Savitha M Rao
*Assistant Examiner* — Taina D Matos Negron
(74) *Attorney, Agent, or Firm* — McKinney Law Group APC; Jeffrey A. McKinney

(57) ABSTRACT

The present invention is directed to methods and compositions for the treatment of diverticulosis. It is more specifically directed to compositions including L-glutamine, its salts, or its derivatives, and uses of such compositions in the treatment of diverticulosis. In a method aspect, the present invention provides a method of treating diverticulosis. The method includes ingestion of 0.05 g/kg body weight to 10.0 g/kg body weight of L-glutamine, an L-glutamine salt or an L-glutamine derivative per day by a person who has diverticulosis.

5 Claims, 1 Drawing Sheet

1

2

METHODS AND COMPOSITIONS FOR THE TREATMENT OF DIVERTICULOSIS

This application is a continuation of U.S. patent application Ser. No. 13/694,592, filed Dec. 14, 2012, which claims priority benefit of U.S. Provisional Patent Application No. 61/630,831, filed Dec. 19, 2011. The entire content of these applications is hereby incorporated by reference herein in its entirety.

FIELD OF THE INVENTION

The present invention is directed to methods and compositions for the treatment of diverticulosis. It is more specifically directed to compositions including L-glutamine, its salts, or its derivatives, and uses of such compositions in the treatment of diverticulosis.

BACKGROUND OF THE INVENTION

Diverticulosis refers to a condition where pouches (i.e., diverticula) form along the colon wall. The pouches are typically 5 to 10 millimeters in diameter and are formed in approximately 50 percent of individuals 60 years old or older.

The etiology of diverticulosis is not well understood. Current theory focuses on observed nutritional differences between cultures: Those cultures that eat a high fiber diet (e.g., Asia and Africa) have a very low incidence of diverticulosis; those that eat a low fiber diet (e.g., United States and Europe) have a high incidence of diverticulosis. Certain physicians believe that the colon of a person eating a diet low in fiber must exert more pressure than usual to move waste through his colon. The relative high pressure distorts weak spots in the colon where blood vessels pass through the muscle layer of the bowel wall, thereby forming pouches.

Many cases of diverticulosis go undiscovered, because the condition alone does not cause symptoms. Diverticulosis is typically diagnosed after a patient experiences complications, such painful diverticular disease or diverticulitis. In other cases, it is discovered during a screening examination (e.g., colonoscopy).

Diverticulosis is usually treated using a combination of nutritional guidelines and medication. A patient may follow a diet regimen involving ingestion of high fiber foods with the objective of consuming 30 to 35 grams of fiber per day. Antispasmodic drugs may be prescribed to relax muscles around the digestive tract. Painkillers may be administered where diverticulitis or other complications of diverticulosis have occurred.

There is a need in the art for additional compositions and methods that can be used to treat diverticulosis. That is an object of the present invention.

SUMMARY OF THE INVENTION

The present invention is directed to methods and compositions for the treatment of diverticulosis. It is more specifically directed to compositions including L-glutamine, its salts, or its derivatives, and uses of such compositions in the treatment of diverticulosis.

In a method aspect, the present invention provides a method of treating diverticulosis. The method includes ingestion of 0.05 g/kg body weight to 10.0 g/kg body weight of L-glutamine, an L-glutamine salt or an L-glutamine derivative per day by a person who has diverticulosis.

In a composition aspect, the present invention provides acomposition for treating diverticulosis. The composition includes L-glutamine, an L-glutamine salt or an L-glutamine derivative and a fiber supplement.

DETAILED DESCRIPTION OF THE INVENTION

The present invention is directed to methods and compositions for the treatment of diverticulosis. It is more specifically directed to compositions including L-glutamine, its salts, or its derivatives, and uses of such compositions in the treatment of diverticulosis.

Figure 1:
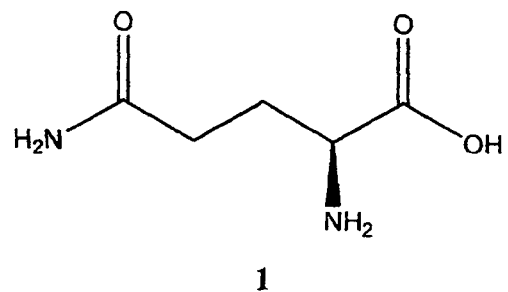
FIG. 1 shows L-glutamine (1) and L-glutamine salts and derivatives (2).
Figure 1:
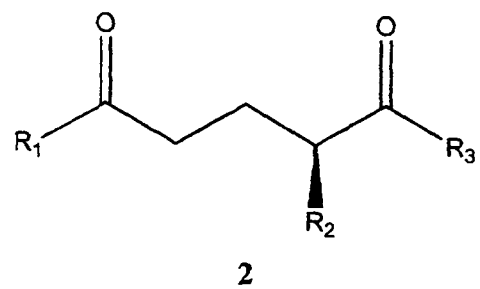

The structure of L-glutamine is shown in FIG. 1, compound 1. L-glutamine salts and derivatives are shown as compound 2 in FIG. 1. Nonlimiting L-glutamine salts and derivatives have the following substituents in reference to compound 2:

$R_1$ is $NH_2$;

$R_2$ is $NH_2$, $NH_3^+$, $NH_3Br$, $NH_3OPO_3H$, $NH_3OC(O)CH_3$ (i.e., acetate salt), $NH_3OC(O)CHCHCO_2H$ (i.e., fumarate salt—trans olefin), $NH_3OC(O)CH(OH)CH(OH)CO_2H$ (i.e., tartrate salt), $NH_3OC(O)CHCHCO_2H$ (i.e., maleate salt—cis olefin), $NH_3OC(O)CH_2$—$C(OH)(CO_2H)CH_2CO_2H$ (i.e., citrate salt), $NH_3OC(O)CO_2H$ (i.e., oxalate salt), $NH_3OS(O)_2OH$ (i.e., methanesulfonate salt), $NH_3OS(O)_2C_6H_4CH_3$ (i.e., p-toluenesulfonate salt), and, $NH_3OC(O)C(O)CH_2CH_2CO_2H$ (i.e., alpha-ketoglutarate salt).

$R_3$ is OH, O⁻, ONa, OK, OCa, OLi, $ONH_2(CH_2C_6H_5)CH_2CH_2NHCH_2C_6H_6$ (i.e., benzathine salt), $ON(CH_2CH_3)_2CH_2CH_2OC(O)C_6H_3ClNH_2$ (i.e., chloroprocaine salt), $ON(CH_3)_3CH_2CH_2OH$ (i.e., choline salt), $ONH_2(CH_2CH_2OH)_2$ (i.e., diethanolamine salt), $ONH_3CH_2CH_2OH$ (i.e., ethanolamine salt), $ONH_3CH_2CH_2NH_2$ (i.e., ethyldiamine salt), $ONH_2(CH_3)CH_2CH(OH)CH(OH)CH(OH)CH(OH)CH_2OH$ (i.e., meglumine salt), $ONH_3C(CH_2OH)_3$ (i.e., tromethamine salt), $ONH_3C(CH_3)_3$ (i.e., tertiary-butylamine salt), $ON(CH_2CH_3)_2CH_2CH_2OC(O)C_6H_4NH_2$ (i.e., procaine salt), $NHCH(CH_3)CO_2H$, $NHCH(CH(CH_3)_2)CO_2H$, NHCH $(CH(CH_3)(CH_2CH_3))CO_2H$, $NHCH(CH_2CH(CH_3)_2)CO_2H$, $NHCH(CH_2CH_2SCH_3)CO_2H$, $NHCH(CH_2C_6H_5)CO_2H$, $NHCH(CH_2C_6H_5OH)CO_2H$, $NHCH(CH_2C_8H_6N)CO_2H$, $NHCH_2CO_2H$, $NHCH(CH_2CH_2C(O)NH_2)CO_2H$, NHCH $(CH_2C(O)NH_2)CO_2H$, $NHCH(CH(OH)CH_3)CO_2H$, NHCH $(CH_2OH)CO_2H$, $NHCH(CH_2CH_2CO_2H)CO_2H$, NHCH $(CH_2CO_2H)CO_2H$.

Typically, a single compound (e.g., L-glutamine) is administered to a person seeking treatment for diverticulosis. In certain cases, however, a mixture of two or more compounds may be administered. For instance, L-glutamine may be administered with one or more L-glutamine salts or derivatives.

L-glutamine, its salts, derivatives or mixtures may be administered in any suitable way. For example, in certain cases it is administered as an aqueous solution. The solution may only have L-glutamine, salts or derivatives as dissolved ingredients, or it may include other pharmaceutically acceptable compounds. Nonlimiting examples of such compounds include buffers and flavorants.

Other, non-limiting examples of ways in which L-glutamine, its salts, derivatives or mixtures may be administered include: as a suspension in a liquid (e.g., water or juice); as a solid, either as a powder or in another form (e.g., pill or capsule); as a mixture with food (e.g., yogurt). As with the aqueous solution, the preceding administration forms may include other pharmaceutically acceptable ingredients.

The amount of L-glutamine, salts or derivatives administered according to the present invention typically range from 0.05 g/kg body weight to 10.0 g/kg-body weight. Oftentimes, the amount ranges from 0.10 g/kg body weight to 8.0 g/kg body weight. In certain cases, the amount ranges from 0.15 g/kg body weight to 7.0 g/kg body weight.

L-glutamine, its salts or derivatives are typically administered to a person once per day. The compounds may, however, be administered more than once per day where indicated.

Where compositions of the present invention are used to treat diverticulosis, they may be combined with other methods used to treat diverticulosis. For instance, the compositions may be administered as part of a dietary regimen focused on the inclusion of increased fiber.

Compositions of the present invention may also be administered and/or combined with a fiber supplement such as CITRUCEL, BENEFIBER and METAMUCIL. The fiber supplement may include soluble and/or insoluble fiber, or the supplement may be entirely composed of soluble and/or insoluble fiber. Nonlimiting examples of fiber with which the compositions can be combined include: methylcellulose; wheat dextrin natural soluble fiber; and, psyllium fiber. The fiber may also include combinations of the foregoing types of fibers.

Combinations of the compositions and fiber may be of any suitable form. The combination may be, for example, in the form of a powder, a capsule, a caplet, a chewable tablet. It may also be included in other supplement forms, such as drinks or gels.

Compositions according to the present invention may be used to treat diverticulosis as determined by a number of different methods to image colon pouches. Nonlimiting examples of imaging methods include: colonoscopy; computed tomography; and, x-ray based on a barium enema.

After administration of L-glutamine, its salts or derivatives for three months, four months, five months, six months, seven months, eight months, nine months, ten months, eleven months or twelve months, the number of pouches observed in a patient's colon have been reduced by at least twenty-five (25) percent. In certain cases, the number of pouches have been reduced by at least fifty (50) percent or seventy-five (75) percent. In other cases, the number of pouches have been reduced by at least eighty (80) percent, eighty-five (85) percent, ninety (90) percent, or ninety-five (95) percent.

Experimental Results

A person had a number of diverticula as observed by colonoscopy. The person ingested 30 g of L-glutamine per day as an aqueous solution. After twelve months of L-glutamine administration, the number of diverticula had been reduced by ninety (90) percent.

The invention claimed is:

1. A method of treating diverticulosis, wherein the method consists of ingestion of 0.05 g/kg body weight to 10.0 g/kg body weight of L-glutamine or an L-glutamine salt per day by a person who has diverticulosis, wherein L-glutamine or an L-glutamine salt is the only active ingredient in a suspension or solution, and wherein the person who has diverticulosis has a number of diverticula, and wherein the number of diverticula in the person with diverticulosis is reduced by at least twenty-five percent.

2. The method according to claim 1, wherein the compound ingested is L-glutamine.

3. The method according to claim 2, wherein the L-glutamine is ingested as part of an aqueous solution or suspension.

4. The method according to claim 2, wherein the L-glutamine is ingested for a period of at least three months.

5. The method according to claim 2, wherein the number of diverticula in the person with diverticulosis is reduced by at least fifty percent.

* * * * *